United States Patent
Pfefferle et al.

(10) Patent No.: US 6,185,945 B1
(45) Date of Patent: Feb. 13, 2001

(54) ISOLATED REFRIGERANT IDENTIFIER

(75) Inventors: Dean P. Pfefferle, Gilberts; Donald G. Huvaere, Palatine, both of IL (US)

(73) Assignee: Snap-on Tools Company, Kenosha, WI (US)

(*) Notice: Under 35 U.S.C. 154(b), the term of this patent shall be extended for 0 days.

(21) Appl. No.: 09/359,184

(22) Filed: Jul. 22, 1999

Related U.S. Application Data

(60) Provisional application No. 60/093,686, filed on Jul. 22, 1998.

(51) Int. Cl.[7] .................................................. F25B 45/00
(52) U.S. Cl. .................................................. 62/149; 62/77
(58) Field of Search ................................. 62/149, 77, 292

(56) References Cited

U.S. PATENT DOCUMENTS

| | | |
|---|---|---|
| Re. 32,451 | 7/1987 | Proctor et al. . |
| 2,464,563 * | 3/1949 | Doeg ........................ 62/115 |
| 2,883,834 | 4/1959 | McAshan, Jr. . |
| 4,285,206 | 8/1981 | Koser . |
| 4,638,973 * | 1/1987 | Torrence ................... 251/129.02 |
| 4,909,042 | 3/1990 | Proctor et al. . |
| 4,938,031 | 7/1990 | Manz et al. . |
| 5,036,675 | 8/1991 | Anderson, Jr. . |
| 5,080,132 * | 1/1992 | Manz et al. ................ 137/614.04 |
| 5,086,630 | 2/1992 | Van Steenburgh, Jr. . |
| 5,095,713 | 3/1992 | Laukhuf et al. . |
| 5,097,667 | 3/1992 | Gramkow . |
| 5,168,721 | 12/1992 | Hancock et al. . |
| 5,335,512 | 8/1994 | Hancock et al. . |
| 5,339,862 * | 8/1994 | Haunhorst ................ 137/614.05 |
| 5,493,869 | 2/1996 | Shirley et al. . |
| 5,582,019 | 12/1996 | Hanna et al. . |
| 5,603,223 | 2/1997 | Murray et al. . |
| 5,617,731 | 4/1997 | Scaringe . |
| 5,758,506 | 6/1998 | Hancock et al. . |
| 5,802,859 | 9/1998 | Zugibe . |
| 5,806,328 | 9/1998 | Muston et al. . |
| 5,875,638 | 3/1999 | Tinsler . |

FOREIGN PATENT DOCUMENTS

| | | | |
|---|---|---|---|
| 4-93566A * | 3/1992 | (JP) ........................... | 62/77 |
| 4728554 * | 3/1992 | (EP) ........................... | 62/149 |

* cited by examiner

*Primary Examiner*—William Doerrler
*Assistant Examiner*—Melvin Jones
(74) *Attorney, Agent, or Firm*—Seyfarth Shaw

(57) ABSTRACT

A refrigerant handling system includes a cabinet having two service ports and two sample ports and housing recycling/recharging apparatus coupled to the service ports and a refrigerant identifier coupled to one of the sample ports and coupled through solenoid-actuated valves to the recharging/recycling apparatus. Two coupling assemblies are provided for coupling the cabinet to the high-pressure and low-pressure sides, respectively, of an automotive air conditioner, each coupling assembly including a service hose with end couplers for respectively coupling to the air conditioner and one of the service ports and connected through solenoid-actuated valves disposed within a housing closely adjacent to the air conditioner coupler. Each coupling assembly also has a sample hose communicating with the service hose within the housing between the air conditioner coupler and the valves and having a distal end with a coupler for connection to one of the sample ports, and electrical conductors for control of the valves.

19 Claims, 3 Drawing Sheets

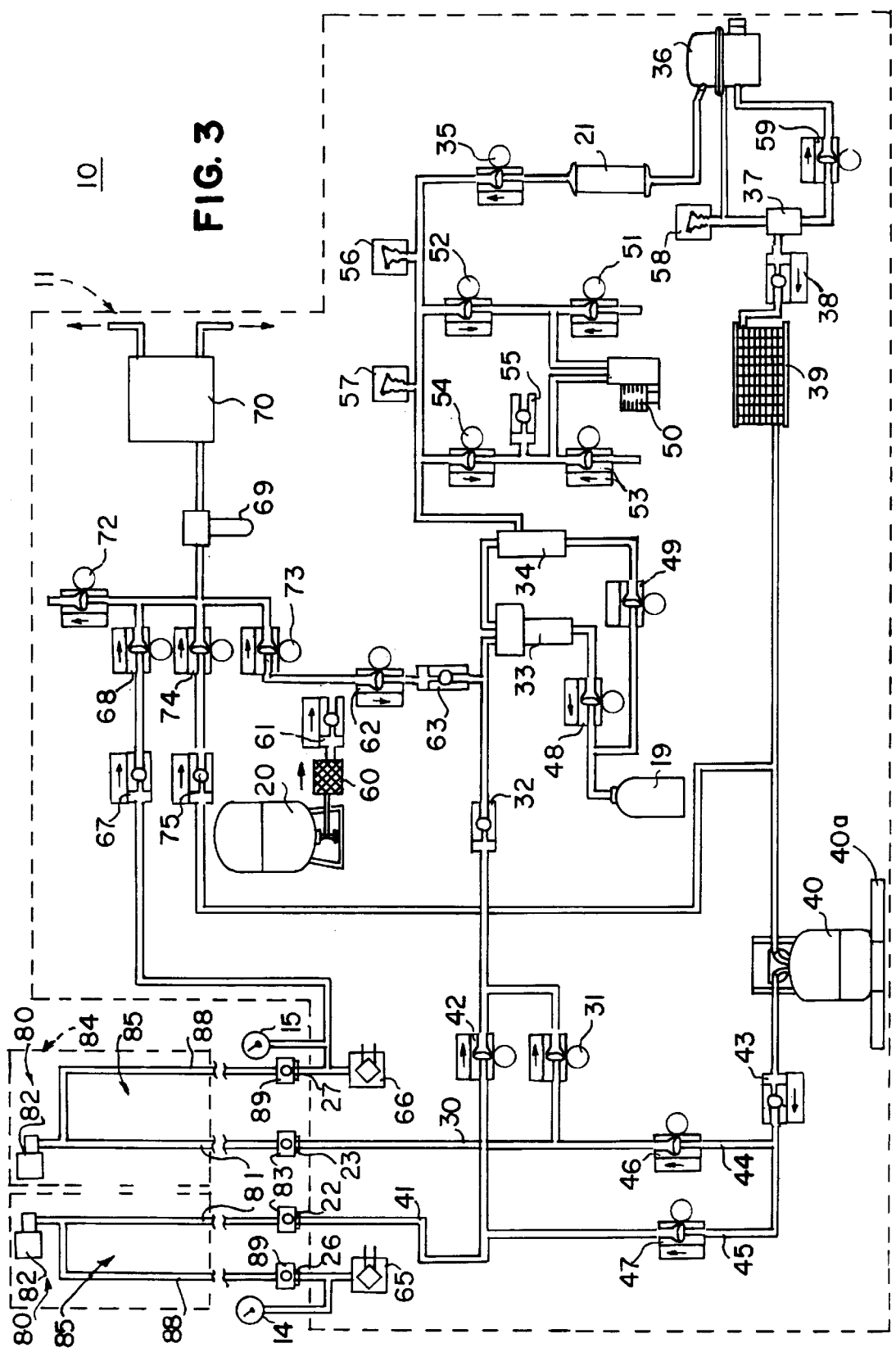

ISOLATED REFRIGERANT IDENTIFIER

CROSS REFERENCE TO RELATED APPLICATION

This application claims the benefit of U.S. provisional application Ser. No. 60/093,686, filed Jul. 22, 1998.

BACKGROUND OF THE INVENTION

The invention relates to refrigerant handling systems for recycling refrigerant from and recharging refrigerant to a refrigeration unit. The invention has particular application to systems of the type designed for servicing automotive air conditioners and which include a refrigerant identifier.

Refrigerant handling systems for servicing automotive air conditioners are well known. Such systems typically can be operated to recover or remove refrigerant from an air conditioner to permit servicing of the air conditioner, to recycle the recovered refrigerant by removing various contaminants therefrom, and then to recharge the refrigerant to the air conditioner after servicing is completed. Such systems are typically connected to an automotive air conditioner by two hoses, respectively connected to the high-pressure and low-pressure sides of the air conditioner compressor. These hoses have a predetermined fixed length sufficient to permit them to reach the air conditioner when the refrigerant rehandling unit is positioned alongside the vehicle.

Several different types of refrigerants are commonly used in automotive air conditioners. It is important that these refrigerants not be contaminated by contact with one another or with other types of contaminants. Thus, identifiers are used to identify the type of refrigerant in the air conditioner and its purity level. A given refrigerant handling system is typically used with only one type of refrigerant, and the identifier determines whether the refrigerant being recovered from the vehicle is of the proper type and purity.

However, in such prior systems, the identifier is coupled in the recovery path and, in the event that the identified refrigerant is of the wrong type or is contaminated, the plumbing of the refrigerant handling system has already been contaminated. In this event, such prior systems would have to be shut down, disconnected from the vehicle and then connected to a separate scavenging unit to clear the system by removing the contamination.

Also, certain automotive manufacturer service specifications specify the precise amount of refrigerant to be recharged to the air conditioner after it is serviced, which amount must be accurate within a tolerance level, such as one ounce. The amount recharged is determined by comparing the weights of the refrigerant tank before and after recharge. But this only determines the amount which has left the recovery tank, and that amount will differ from the amount which enters the air conditioner by the amount left in the intervening conduits and hoses. Thus, the refrigerant handling system recharge protocol must compensate for this difference, and must also compensate for ambient conditions, such as temperature and pressure, which can affect the volume of the refrigerant. This compensation requires the use of very complicated algorithms in the system processor during the calibration procedure. This effectively precludes varying the length of the service hoses between the refrigerant handling system and the air conditioner, since every time the hose length is changed the system would have to be recalibrated and/or the software algorithm would have to be changed.

SUMMARY OF THE INVENTION

It is a general object of the invention to provide an improved refrigerant handling system, which avoids the disadvantages of prior systems while affording additional structural and operating advantages.

An important feature of the invention is the provision of a refrigerant handling system which permits refrigerant identification and purification determination without risk of contamination of the recycle and recharge plumbing of the system.

In connection with the foregoing feature, another feature of the invention is the provision of a system of the type set forth, which includes a refrigerant identifier isolated from the remainder of the system.

In connection with the foregoing feature, a still further feature of the invention is the provision of a system of the type set forth, which provides a sampling path in parallel with the recycling and recharge paths of the system.

Another important feature of the invention is the provision of a system of the type set forth, which permits more accurate control of the amount of refrigerant recharged to a refrigeration unit.

Yet another feature of the invention is the provision of a system of the type set forth, which permits change of the length of hoses coupling the system to an associated refrigeration unit, without requiring recalibration of the system.

In connection with the foregoing features, a further feature of the invention is the provision of a coupling assembly for coupling a system of the type set forth with an associated refrigeration unit, which provides a sample path in parallel with a service path through remotely controlled valves disposed closely adjacent to the associated refrigeration unit.

Certain ones of these and other features of said invention may be attained by providing in a refrigerant handling system including recycling/recharging apparatus for withdrawing refrigerant from a refrigeration unit, removing contaminants from the refrigerant, and recharging the refrigerant to the refrigeration unit, the improvement comprising: a coupling conduit having a first end with a first coupler for coupling to the recycling/recharging apparatus and a second end with a second coupler for coupling to an associated refrigeration unit, a remotely controllable first valve assembly connected in the coupling conduit closely adjacent to the second end for selectively controlling refrigeration flow through the conduit, a sample unit coupled to the second coupler and including a second remotely controllable valve assembly coupled to the recycling/recharging apparatus for selectively permitting or preventing refrigerant flow between said sample unit and the recycling/recharging apparatus, and a controller connected to the first and second valve assemblies for controlling operation thereof.

Further features of the invention may be attained by providing a coupling assembly for coupling an automotive air conditioner to a refrigerant handling system comprising: a housing, a first conduit passing through the housing and having a first end with a first fluid coupler for coupling to the handling system and a second end with a second fluid coupler for coupling to the air conditioner, an electrically controlled valve assembly coupled in the first conduit and disposed in the housing, electrical conductors electrically connected to the valve assembly for control thereof and having distal ends outside of the housing connected to an electrical connector, a second conduit communicating with the first conduit within the housing between the second fluid coupler and the valve assembly and having a distal end external of the housing, and a third fluid coupler at the distal end of the second conduit.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 3 is a schematic diagram of the fluid circuitry of the system of FIGS. 1 and 2;

DESCRIPTION OF THE PREFERRED EMBODIMENT

Figure 1:
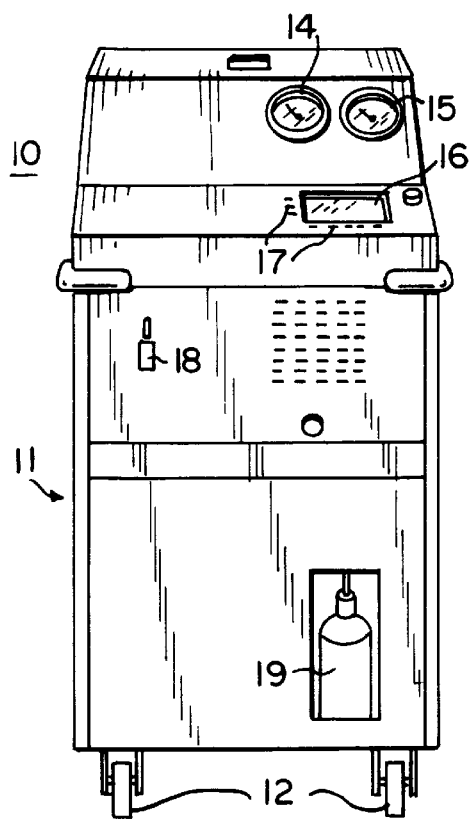
FIG. 1 is front elevational view of the cabinet of a refrigerant handling system in accordance with the present invention.
Figure 2:
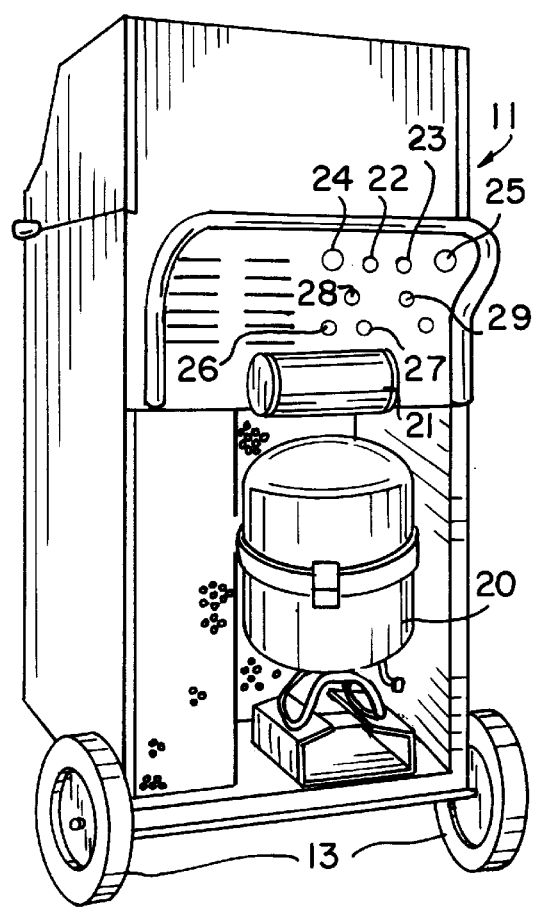
FIG. 2 is a slightly enlarged, rear perspective view of the cabinet of FIG. 1.

Referring to FIGS. 1 and 2, there is illustrated a refrigerant handling system, generally designated by the numeral 10, in accordance with the present invention. The system 10 is housed in a cabinet 11 having a pair of front swivel casters 12 and a pair of rear wheels 13 mounted on a common axle. The system includes a high-pressure gauge 14 and a low-pressure gauge 15, and a display 16, which may be a liquid crystal display, provided with control keys 17, some of which may be soft keys, all visible and accessible by a user. Also visible to a user is a filter 18. An oil drain bottle 19 is disposed in a recess in the front panel, while a virgin refrigerant supply tank 20 is mounted in a recess in the rear of the cabinet 11. Also mounted on the rear of the cabinet is a filter/dryer 21 and a plurality of connection ports, including a high-pressure service port 22, a low-pressure service port 23, vent ports 24 and 25, sample input ports 26 and 27 and electrical connection sockets 28 and 29.

Referring also to FIG. 3, there is illustrated a diagram of the plumbing of the system 10, the cabinet wall being designated by the dashed line 11. The system includes a refrigerant intake line 30, coupled to the low-pressure port 23 and coupled through a solenoid valve 31 and a check valve 32 to the inlet of an oil separator 33, the outlet of which is connected to the inlet of a coalescing filter 34. The outlet of the filter 34 is coupled through a solenoid valve 35 and the filter dryer 21 to the suction port of a compressor 36. The discharge of the compressor 36 is coupled through a coalescing filter 37 and a check valve 38 to a condenser 39, the outlet of which is coupled to the inlet of a refrigerant recovery tank 40, which is disposed on a suitable scale 40a. The system also has a high-pressure intake line 41 coupled to the high-pressure port 22 and also coupled through a solenoid valve 42 to the check valve 32.

The outlet of the recovery tank 40 is coupled through a check valve 43 to two parallel recharge lines 44 and 45, which are respectively coupled through solenoid valves 46 and 47 to the intake lines 30 and 41.

The drains of the oil separator 33 and the coalescing filter 34 are, respectively, coupled through solenoid valves 48 and 49 to the oil drain bottle 19. The system also includes a vacuum pump 50, having an intake coupled to atmosphere through a solenoid valve 51, and to the outlet of the coalescing filter 34 through a solenoid valve 52. The exhaust of the vacuum pump 50 is coupled to atmosphere through a solenoid valve 53 and to the outlet of the coalescing filter 34 through a solenoid valve 54, a relief valve 55 being coupled between the valve 54 and the exhaust of the vacuum pump 50. A vacuum switch 56 is coupled between the solenoid valves 35 and 52, while a low-pressure cutoff switch 57 is coupled between the solenoid valves 52 and 54. A high-pressure cutoff switch 58 is coupled between the discharge of the compressor 36 and the coalescing filter 37. The drain of the filter 37 is coupled back to the compressor through a solenoid valve 59. The refrigerant supply tank 20 is coupled through a filter 60, a check valve 61, a solenoid valve 62 and a check valve 63 to the intake line between the check valve 32 and the inlet of the oil separator 33.

High-pressure and low-pressure transducer 65 and 66 are respectively coupled to the sample ports 26 and 27, which are also respectively coupled to the pressure gauges 14 and 15. The sample port 27 is also coupled through a check valve 67, solenoid valve 68 and a regulator 69 to a sample identifier 70, which may be a non-dispersive infrared identifier, for identifying the type and purity of a sample refrigerant. A solenoid valve 72 is coupled between the input of the regulator 69 and atmosphere. A solenoid 73 is coupled between the solenoid valve 72 and the virgin refrigerant supply line at the output of the check valve 61. A solenoid valve 74 is coupled in series with a check valve 75 between the output of the condenser 39 and the input of the regulator 69.

The operation of the system 10 during refrigerant recovery, recycling and recharge operations are substantially the same as in prior systems and will be well understood by those skilled in the art and, accordingly, will not be discussed in detail herein. One such prior system is sold by Snap-on Technologies, Inc. under the trademark KOOL KARE. It is, however, a significant aspect of the invention that in the system 10 the identifier 70 and the sample path thereto from the low-pressure side of the associated vehicle air conditioning unit may be isolated from the remainder of the system, as will be explained in greater detail below.

Figure 5:
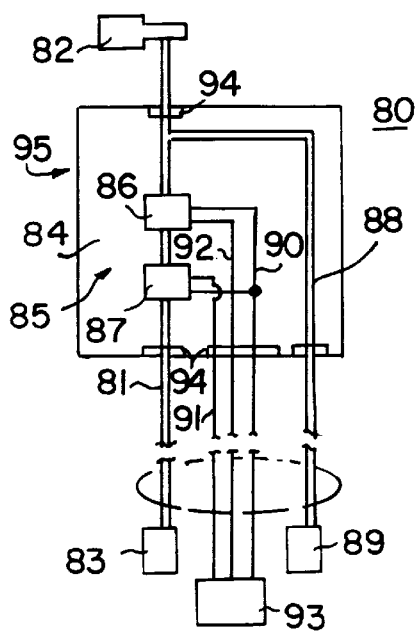
FIG. 5 is a schematic diagram of one the coupling assemblies of the system of the present invention.

Referring now also to FIG. 5, the system 10 is coupled to the high-pressure and low-pressure sides of an associated automotive air conditioner to be serviced (not shown) respectively through two coupling assemblies 80, which are substantially identical in construction, wherefore only one will be described in detail. Each coupling assembly 80 includes an elongated service hose or conduit 81 provided at one end with a fluid coupler 82 adapted to be coupled to one side of the air conditioner of an associated automotive vehicle, and provided at the other end with a fluid coupler 83 adapted to be coupled to one of the service ports 22 or 23. The service hose 81 extends through a housing 84, in which is disposed a valve assembly 85 including two solenoid-actuated valves 86 and 87 connected in series in the service hose 81 for controlling the flow of fluid therethrough. The housing 84 is disposed closely adjacent to the coupler 82, preferably so that the valve assembly 85 is disposed within about one foot of the coupler 82. The overall length of the service hose 81 is sufficient to conveniently span the distance between a vehicle air conditioner and the refrigerant handling system 10 when disposed alongside the vehicle, preferably at least eight feet. The valves 86 and 87 are arranged in back-to-back (output-to-output) configuration, so that when de-energized no flow is possible in either direction through the service hose 81, irrespective of pressure differences. A single valve can be used in place of the valves 86 and 87, provided this requirement is met. The coupling assembly 80 also includes a sample hose or conduit 88 communicating at one with the service hose 81 within the housing 84 between the coupler 82 and the valve 86. The other end of the sample hose 88 is disposed outside the housing 84 and is provided with a fluid coupler 89 adapted for coupling to the sample ports 26 or 27, the sample hose 88 having an overall length approximately the same as that of the service hose 81.

The coupling assembly 80 also includes three electrical conductors 90, 91, and 92 connected at one end to the valves 86 and 87 within the housing 84, and connected at their other ends, outside the housing 84, to a single electrical connector 93, adapted to be coupled a suitable mating connector 28 or 29 on the housing 11. Again, the overall length of the conductors 90–92 is approximately the same as that of the service hose 81. Should a single valve be used in place of valves 86 and 87 only two electrical connectors would be needed. It will be appreciated that the service hose 81, the sample hose 88 and the conductors 90–92 pass through walls of the housing 84 in suitable fittings 94, which may provide strain relief, sealing or other desired functions. The hoses 81 and 88 and conductors 90–92 may be bundled together in any suitable manner between their distal ends and the housing 84.

The housing 84 and its contents define a pod 95, which may include several additional electronic components. More specifically, referring to FIG. 4, the coil of the solenoid valve 86 is connected across the conductors 90 and 92, while the coil of the solenoid valve 87 is connected across the conductors 91 and 92. The conductor 90 is also connected through a resistor 96 to the anode of a diode 97, the cathode of which is connected to the conductor 92. An LED 98 is connected in parallel with the diode 97, the LED 98 having its anode connected to the conductor 92 and being disposed so as to be visible through a suitable opening (not shown) in the housing 84 to provide an indication when the valve assembly 85 is energized or opened to permit flow through the service hose 81.

Figure 4:
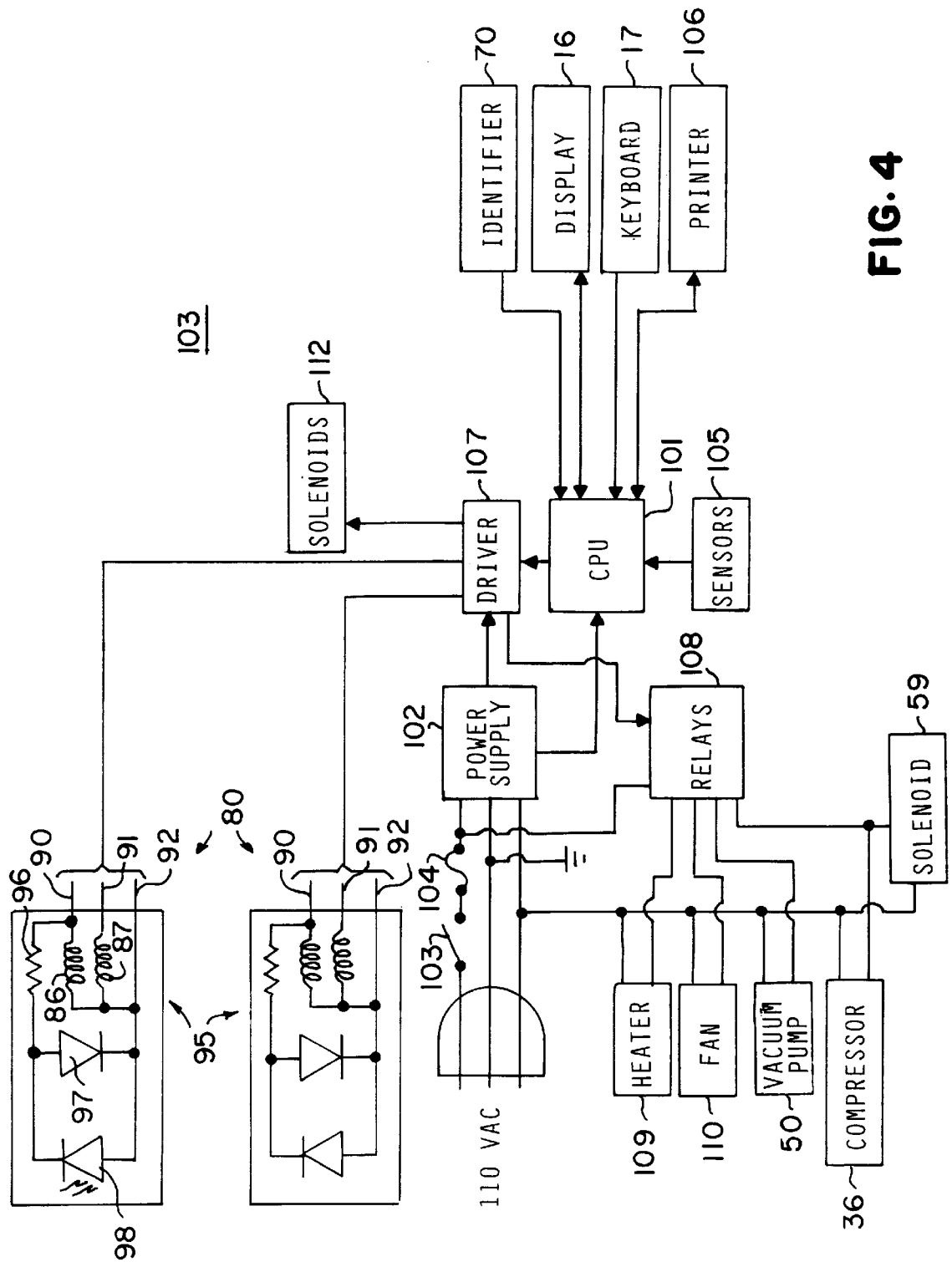
FIG. 4 is a partially schematic and partially functional block diagrammatic view of the electronic control circuitry of the system of FIGS. 1 and 2.

Referring to FIG. 4, there is illustrated the electrical control system for the refrigerant handling system 10, generally designated by the numeral 100. The control system 100 includes a central processing unit 101, which may be a suitable microprocessor, and is powered from a power supply 102 which is coupled to a suitable source of 110 VAC power through an ON/OFF switch 103 and a fuse 104. Sensors 105, which may include the pressure transducers 65 and 66, the scale 40*a*, temperature sensors and the like, are coupled to the CPU 101, as are the display 16, the keyboard 17, the identifier 70 and, optionally, a printer 106. The CPU 101 controls a driver 107 which, in turn, controls the operation of a plurality of relays 108 for respectively controlling a heater 109, the fan 110 of the condenser 39, the vacuum pump 50, and the compressor 36 and drain solenoid 59 thereof. The driver 107 also controls solenoids 112, which include the solenoids for the remainder of the solenoid valves described above. The driver 107 is connected to the sockets 28 and 29 on the rear of the cabinet 11.

Referring again to FIG. 3, in operation, when it is desired to service an automotive air conditioner, the couplers 83 of the coupling assemblies 80 are, respectively, coupled to the service ports 22 and 23, while the sample couplers 89 are respectively coupled to the sample ports 26 and 27, and the connectors 93 are, respectively, connected to the sockets 28 and 29. The couplers 82 are then, respectively, coupled to the high and low sides of the vehicle air conditioner, in a known manner. At this point, the valve assemblies 85 are de-energized, blocking fluid flow through the service hoses 81. However, refrigerant can flow through the sample hoses 88, respectively to the pressure gauges 14 and 15 and the pressure transducers 65 and 66, so that the operator can determine if the pressures are in the proper range. Refrigerant can also flow through the check valve 67 to the solenoid valve 68. It will be appreciated that, at this point, before the system has been activated, all of the solenoid valves are de-energized. The solenoid valves 51, 53 and 72 to atmosphere and the drain valve 59 for the compressor are normally-open valves and, therefore, in this condition will be open, but all of the other solenoid valves will be closed.

If the coupling assemblies 80 are properly connected and the pressures are in the proper range, the operator can initiate an identification routine, opening the solenoid valve 68 and allowing refrigerant to flow to the identifier 70. Before the identifier 70 is activated, valve 68 is held open for about 10 seconds to purge any refrigerant which may remain in the sample path downstream of the check valve 67 from the last identification routine. Then the system 10 will then provide an indication on the display 16 of the identification of the refrigerant in the vehicle and its purity. If the type and/or purity of the air conditioner refrigerant is not compatible with that in the system 10, the operator goes no further and, indeed, the program of the system can be designed to prevent him from doing so. Rather, he then disconnects the couplers from the vehicle air conditioner and places them back on the vent ports 24 and 25 on the cabinet 11, allowing the sample hoses 88 to vent to atmosphere. In this regard, it will be appreciated that only the approximately one-foot length of the service hoses 81 from the couplers 82 to the valve assemblies 85 need be vented, since the refrigerant could not move beyond the valve assemblies 85. The entire identification path can easily be vented and no other part of the system 10 has been contaminated by the vehicle refrigerant.

If, on the other hand, the vehicle refrigerant is of the proper type and purity, the operator can proceed with the recovery, recycling and recharge modes of operation of the system 10 in a normal manner. In this regard, the high-pressure valve assembly 85 will first be opened to permit flow of refrigerant into the system intake line 41 from the high-pressure side of the air conditioner, and, if need be, the other valve assembly 85 can be opened to admit refrigerant from the low-pressure side, all in a well-known manner.

It is another significant aspect of the invention that the coupling assemblies 80 may be provided in varying lengths, which can be substituted for one another without necessitating recalibration of the system 10. This is because, irrespective of the length of the coupling assembly 80, during the recharge operation, the system can be pre-charged all the way up to the valve assemblies 85. Because of the very short length of conduit between the valve assemblies 85 and the vehicle air conditioner, this length of hose, preferably no more than about one foot, can only hold a very small amount of refrigerant, e.g., about one-half ounce. Since a typical manufacturer's specification requires line compensation accuracy only to about one ounce, atmospheric conditions cannot affect the small amount of refrigerant in the hoses enough to exceed this tolerance limit. Therefore, the system software can be programmed to simply charge the prescribed amount plus the small amount in the service hoses 81 between the air conditioner and the valve assemblies 85, thereby greatly increasing the accuracy of the recharge.

While the valve assembly 85 has been shown as including two one-way valves, it will be appreciated that a single valve could also be utilized.

From the foregoing, it can be seen that there has been provided an improved refrigerant handling system which provides refrigerant identification without risk of contamination of recovery, recycling and recharge plumbing, provides improved accuracy of refrigerant recharge and permits changing of the length of the service hoses without necessitating recalibration of the system.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. In a refrigerant handling system including recycling/recharging apparatus for withdrawing refrigerant from a refrigeration unit, removing contaminants from the refrigerant, and recharging the refrigerant to the refrigeration unit, the improvement comprising:
    a coupling conduit having a first end with a first coupler for coupling to the recycling/recharging apparatus and a second end with a second coupler for coupling to an associated refrigeration unit,
    a remotely controllable first valve assembly connected in said coupling conduit closely adjacent to said second end for selectively controlling refrigeration flow through the conduit,
    a sample unit coupled to the second coupler and including a second remotely controllable valve assembly coupled to the recycling/recharging apparatus for selectively permitting or preventing refrigerant flow between the sample unit and the recycling/recharging apparatus, and
    a controller connected to said first and second valve assemblies for controlling operation thereof.

2. The system of claim 1, wherein each of said valve assemblies is solenoid-actuated.

3. The system of claim 2, wherein said first valve assembly includes two valves connected output-to-output.

4. The system of claim 1, and further comprising a housing enclosing the recycling/recharging apparatus, said coupling conduit and said first valve assembly being disposed externally of said housing.

5. The system of claim 1, wherein said sample unit includes a refrigerant identifier.

6. The system of claim 5, wherein said second valve assembly is solenoid-actuated.

7. The system of claim 1, wherein said controller includes a microprocessor operating under stored program control.

8. In a refrigerant handling system including recycling/recharging apparatus for withdrawing refrigerant from a refrigerant unit having high-pressure and low-pressure ports, removing contaminants from the refrigerant, and recharging the refrigerant to the refrigeration unit, the improvement comprising:
    two coupling assemblies for respectively coupling said high-pressure and low-pressure ports to the recycling/recharging apparatus;
    each of said coupling assemblies including:
        a coupling conduit having a first end with a first coupler for coupling to the recycling/recharging apparatus and a second end with a second coupler for coupling to an associated refrigeration unit,
        a remotely controllable first valve assembly connected in said coupling conduit closely adjacent to said second end for selectively controlling refrigeration flow through the conduit, and
        a sample line communicating with the second coupler and having a distal end with a sample coupler;
    a sample unit coupled to the sample coupler of one of the coupling assemblies and including a second remotely controllable valve assembly coupled to the recycling/recharging apparatus for selectively permitting or preventing refrigerant flow between the sample unit and the recycling/recharging apparatus; and
    a controller connected to said first and second valve assemblies for controlling operation thereof.

9. The system of claim 8, and further comprising pressure gauges respectively coupled to the sample couplers of said coupling assemblies.

10. The system of claim 8, wherein said sample unit includes a refrigerant identifier.

11. The system of claim 10, wherein each of said first and second valve assemblies is solenoid-actuated.

12. The system of claim 11, wherein said controller includes a microprocessor operating under stored program control.

13. The system of claim 8, and further comprising a housing enclosing the recycling/recharging apparatus, said coupling conduit and said first valve assembly being disposed externally of said housing.

14. The system of claim 13, wherein said housing includes receptacles for supporting said second couplers in communication with the atmosphere when said second couplers are not connected to the associated refrigeration unit.

15. The system of claim 8, wherein each of said coupling assemblies includes a housing enclosing he first valve assembly.

16. A coupling assembly for coupling an automotive air conditioner to a refrigerant handling system comprising:
    a housing,
    a first conduit passing through the housing and having a first end with a first fluid coupler for coupling to the handling system and a second end with a second fluid coupler for coupling to the air conditioner,
    an electrically controlled valve assembly coupled in said first conduit and disposed in said housing,
    electrical conductors electrically connected to said valve assembly for control thereof and having distal ends outside of said housing connected to an electrical connector,
    a second conduit communicating with said first conduit within said housing between said second fluid coupler and said valve assembly and having a distal end external of said housing, and
    a third fluid coupler at said distal end of said second conduit.

17. The coupling assembly of claim 16, wherein said valve assembly is solenoid-actuated.

18. The coupling assembly of claim 17, wherein said valve assembly includes two valves connected back-to-back.

19. The coupling assembly of claim 16, and further comprising means bundling said first and second conduits and said electrical conductors between said housing and the refrigerant handling system.

* * * * *

UNITED STATES PATENT AND TRADEMARK OFFICE
CERTIFICATE OF CORRECTION

PATENT NO.    : 6,185,945 B1
DATED         : February 13, 2001
INVENTOR(S)   : Pfefferle et al.

Page 1 of 1

It is certified that error appears in the above-identified patent and that said Letters Patent is hereby corrected as shown below:

<u>Title page,</u>
Item [56] References Cited, FOREIGN PATENT DOCUMENTS, "4728554" should be -- 472854 --.

Signed and Sealed this

Second Day of October, 2001

Attest:

*Nicholas P. Godici*

NICHOLAS P. GODICI
*Acting Director of the United States Patent and Trademark Office*

*Attesting Officer*

UNITED STATES PATENT AND TRADEMARK OFFICE
CERTIFICATE OF CORRECTION

PATENT NO. : 6,185,945 B1 Page 1 of 1
APPLICATION NO. : 09/359184
DATED : February 13, 2001
INVENTOR(S) : Pfefferle et al.

It is certified that error appears in the above-identified patent and that said Letters Patent is hereby corrected as shown below:

Title Page,
item (56) References Cited, FOREIGN PATENT DOCUMENTS,
"4728554" should be -- 472854 --.

Signed and Sealed this

Twelfth Day of February, 2008

JON W. DUDAS
*Director of the United States Patent and Trademark Office*